(12) United States Patent
Kalender et al.

(10) Patent No.: US 7,924,974 B2
(45) Date of Patent: Apr. 12, 2011

(54) X-RAY MACHINE FOR BREAST EXAMINATION IN A STANDING POSITION

(75) Inventors: Willi Kalender, Moehrendorf (DE); Harry Schilling, Eichstaett (DE)

(73) Assignee: MIR Medical Imaging Research Holding GmbH, Moehrendorf (DE)

( * ) Notice: Subject to any disclaimer, the term of this patent is extended or adjusted under 35 U.S.C. 154(b) by 0 days.

(21) Appl. No.: 12/401,735

(22) Filed: Mar. 11, 2009

(65) Prior Publication Data

US 2010/0080343 A1    Apr. 1, 2010

(30) Foreign Application Priority Data

Sep. 29, 2008  (DE) .......................... 10 2008 042 430

(51) Int. Cl.
*A61B 6/04*  (2006.01)
*H05G 1/02*  (2006.01)
(52) U.S. Cl. .......................................... 378/37; 378/208
(58) Field of Classification Search ................... 378/37, 378/208
See application file for complete search history.

(56) References Cited

U.S. PATENT DOCUMENTS

| | | | |
|---|---|---|---|
| 3,673,394 A | 6/1972 | Hartmann | |
| 4,015,836 A | 4/1977 | Redington et al. | |
| 4,400,827 A | 8/1983 | Spears | |
| 4,680,028 A | 7/1987 | Stuart | |
| 4,709,382 A | 11/1987 | Sones | |
| 5,273,435 A | 12/1993 | Jacobson | |
| 5,308,321 A | 5/1994 | Castro | |
| 5,386,447 A | 1/1995 | Siczek | |
| 5,426,685 A | 6/1995 | Pellegrino et al. | |
| 5,528,043 A | 6/1996 | Spivey et al. | |
| 5,569,266 A | 10/1996 | Siczek | |
| 5,609,827 A | 3/1997 | Russell et al. | |
| 5,664,569 A | 9/1997 | Damadian et al. | |
| 5,757,878 A | 5/1998 | Dobbs et al. | |
| 5,803,912 A | 9/1998 | Siczek et al. | |
| 6,242,743 B1 | 6/2001 | DeVito et al. | |
| 6,254,614 B1 | 7/2001 | Jesseph | |

(Continued)

FOREIGN PATENT DOCUMENTS

DE       19639975        5/1998

(Continued)

OTHER PUBLICATIONS

Mun et al., "Active RFID System Augmented with 2D Barcode for Asset Management in a Hospital Setting," IEEE International Conference on RFID, Mar. 2007, pp. 205-211.

(Continued)

*Primary Examiner* — Edward J Glick
*Assistant Examiner* — Anastasai Midkiff
(74) *Attorney, Agent, or Firm* — Kevin L. Daffer; Daffer McDaniel, LLP

(57) ABSTRACT

An X-ray machine for imaging a female breast has a support with an attached continuously rotatable gantry. An X-ray tube with an oppositely located X-ray detector is mounted on the gantry. A locating means for accommodating a breast is disposed coaxially with a rotation axis of the gantry. The gantry is adapted to be moved relative to the locating means by an advancing means. In order to achieve a high throughput of patients, a locating means having an opening for accommodating a breast is provided relative to both sides of the gantry. The X-ray machine may be incorporated between two separating walls which have cut-out portions for the locating means.

18 Claims, 4 Drawing Sheets

U.S. PATENT DOCUMENTS

| | | | |
|---|---|---|---|
| 6,298,114 B1 | 10/2001 | Yoda | |
| 6,325,537 B1 | 12/2001 | Watanabe | |
| 6,358,246 B1 | 3/2002 | Behl et al. | |
| 6,415,012 B1 | 7/2002 | Taguchi et al. | |
| 6,418,188 B1 | 7/2002 | Broadnax | |
| 6,419,390 B1 * | 7/2002 | Landis-Lowell | 378/209 |
| 6,463,122 B1 | 10/2002 | Moore | |
| 6,480,565 B1 * | 11/2002 | Ning | 378/37 |
| 6,684,097 B1 | 1/2004 | Parel et al. | |
| 6,819,736 B1 | 11/2004 | Bruder et al. | |
| 6,837,772 B1 | 1/2005 | Luk | |
| 6,872,001 B1 | 3/2005 | Gilevich | |
| 7,005,988 B2 | 2/2006 | Mathewson, II et al. | |
| 7,065,393 B2 | 6/2006 | Sati et al. | |
| 7,304,578 B1 | 12/2007 | Sayers et al. | |
| 7,453,978 B1 | 11/2008 | DiBianca et al. | |
| 7,467,892 B2 | 12/2008 | Lang et al. | |
| 7,492,858 B2 | 2/2009 | Partain et al. | |
| 7,556,426 B2 | 7/2009 | Nakajo et al. | |
| 7,558,370 B2 | 7/2009 | Sommer, Jr. et al. | |
| 7,677,799 B2 | 3/2010 | Jensen et al. | |
| 7,697,660 B2 | 4/2010 | Ning | |
| 7,743,953 B2 | 6/2010 | Okazaki et al. | |
| 7,764,765 B2 | 7/2010 | Ohta et al. | |
| 2002/0181651 A1 | 12/2002 | Shepherd et al. | |
| 2003/0072409 A1 | 4/2003 | Kaufhold et al. | |
| 2003/0204965 A1 | 11/2003 | Hennessey | |
| 2004/0066880 A1 | 4/2004 | Oikawa | |
| 2004/0082856 A1 | 4/2004 | Marmarelis | |
| 2004/0092826 A1 | 5/2004 | Corbeil et al. | |
| 2004/0238750 A1 | 12/2004 | Vafi et al. | |
| 2004/0251419 A1 | 12/2004 | Nelson et al. | |
| 2004/0254461 A1 | 12/2004 | Ackerman, III | |
| 2005/0070817 A1 | 3/2005 | Mueller, Jr. | |
| 2006/0094950 A1 | 5/2006 | Ning | |
| 2006/0145871 A1 | 7/2006 | Donati et al. | |
| 2006/0262898 A1 * | 11/2006 | Partain et al. | 378/37 |
| 2007/0009080 A1 | 1/2007 | Mistretta | |
| 2007/0064867 A1 | 3/2007 | Hansen et al. | |
| 2007/0092059 A1 | 4/2007 | Eberhard et al. | |
| 2007/0237306 A1 | 10/2007 | Jones et al. | |
| 2007/0238957 A1 | 10/2007 | Yared | |
| 2008/0033420 A1 | 2/2008 | Nields et al. | |
| 2008/0037703 A1 * | 2/2008 | Ting | 378/37 |
| 2008/0081984 A1 | 4/2008 | Lafferty | |
| 2008/0084961 A1 | 4/2008 | Keppel et al. | |
| 2008/0089471 A1 | 4/2008 | Kobayashi | |
| 2008/0101538 A1 | 5/2008 | Schliermann | |
| 2008/0187095 A1 | 8/2008 | Boone et al. | |
| 2008/0205588 A1 | 8/2008 | Kim | |
| 2008/0221443 A1 | 9/2008 | Ritchie et al. | |
| 2008/0221478 A1 | 9/2008 | Ritchie et al. | |
| 2008/0230074 A1 | 9/2008 | Zheng et al. | |
| 2009/0080604 A1 | 3/2009 | Shores et al. | |
| 2009/0196393 A1 | 8/2009 | Wang et al. | |
| 2010/0080344 A1 | 4/2010 | Schilling et al. | |
| 2010/0080345 A1 | 4/2010 | Schilling et al. | |
| 2010/0080346 A1 | 4/2010 | Kalender et al. | |
| 2010/0080347 A1 | 4/2010 | Kalender et al. | |
| 2010/0080348 A1 | 4/2010 | Kalender et al. | |
| 2010/0080349 A1 | 4/2010 | Kalender et al. | |
| 2010/0080350 A1 | 4/2010 | Kalender et al. | |
| 2010/0128843 A1 | 5/2010 | Tita | |

FOREIGN PATENT DOCUMENTS

| | | |
|---|---|---|
| DE | 19812995 | 10/1999 |
| DE | 10026792 | 12/2001 |
| DE | 10207623 | 11/2003 |
| DE | 102004042790 | 3/2006 |
| DE | 102005022347 | 11/2006 |
| DE | 102005048049 | 4/2007 |
| EP | 0435837 | 7/1991 |
| EP | 1549115 | 6/2005 |
| EP | 1700568 | 9/2006 |
| EP | 1864611 | 12/2007 |
| JP | 2008272093 | 11/2008 |
| WO | 93/17620 | 9/1993 |
| WO | 94/06352 | 3/1994 |
| WO | 98/49939 | 11/1998 |
| WO | 99/30615 | 6/1999 |
| WO | 2004/006755 | 1/2004 |
| WO | 2004/043535 | 5/2004 |
| WO | 2006/119426 | 11/2006 |
| WO | 2007/120622 | 10/2007 |
| WO | 2008/024611 | 2/2008 |
| WO | 2008/054279 | 5/2008 |

OTHER PUBLICATIONS

Nishide et al., "Micro-focus x-ray CT imaging of breast specimens with microcalcifications," 89th Scientific Assembly and Annual Meeting of the Radiological Society of North America, Dec. 2003, pp. 1662-1663.

Tornai et al., "Design and Development of a Fully-3D Dedicated X-ray Computed Mammotomography System," Proceedings of SPIE, vol. 5745, 2005, pp. 189-197.

Bentzen et al., "Isotherm mapping in hyperthermia using subtraction X-ray computed tomography," Radiotherapy and Oncology, vol. 2, 1984, pp. 255-260.

Griffiths et al., "Applied potential tomography for non-invasive temperature mapping in hyperthermia," Clin. Phys. Physiol. Meas., vol. 8, Suppl. A, 1987, pp. 147-153.

Jenne et al, "CT On-Line Monitoring of HIFU Therapy," IEEE Ultrasonics Symposium, 1997, pp. 1377-1380.

Fallone et al., "Noninvasive thermometry with a clinical x-ray CT scanner," Med. Phys., vol. 9, No. 5, 1982, pp. 715-721.

Office Action mailed Nov. 3, 2009 for U.S. Appl. No. 12/401,765.

Notice of Allowance mailed Apr. 15, 2010 for U.S. Appl. No. 12/401,765.

Office Action mailed Apr. 14, 2010 for U.S. Appl. No. 12/402,059.

Office Action mailed Apr. 1, 2010 for U.S. Appl. No. 12/402,141.

Office Action mailed Jul. 13, 2010 for U.S. Appl. No. 12/402,225.

Office Action mailed May 11, 2010 for U.S. Appl. No. 12/401,814.

Notice of Allowance mailed Aug. 23, 2010 for U.S. Appl. No. 12/401,765.

Notice of Allowance mailed Sep. 17, 2010 for U.S. Appl. No. 12/402,059.

Office Action mailed Sep. 23, 2010 for U.S. Appl. No. 12/401,792.

Notice of Allowance mailed Sep. 29, 2010 for U.S. Appl. No. 12/401,814.

* cited by examiner

US 7,924,974 B2

X-RAY MACHINE FOR BREAST EXAMINATION IN A STANDING POSITION

PRIORITY CLAIM

This application claims priority to pending German Application No. DE102008042430.7 filed on Sep. 29, 2008.

BACKGROUND OF THE INVENTION

1. Field of the Invention

The invention relates to an X-ray machine for forming an image of a female breast (mammography). In particular, the invention relates to a machine for performing screening tests efficiently.

2. Description of Related Art

For performing examinations of female breasts, X-ray machines are known in which a person to be examined is positioned on a patient table. A machine of this kind is disclosed, for example, in U.S. Pat. No. 6,480,565. A shortening of examination time is made possible by X-ray machines such as described in U.S. Pat. No. 5,386,447, in which a person to be examined stands in front of the X-ray machine. From U.S. Patent Application Publication No. 2007/0092059 another X-ray machine is known, in which a radiation emitter and a plate-shaped detector can be moved along a semi-circle around a breast to be examined. Here, exposures could be made at various positions from various angles. With this prior art, it is of disadvantage that, on the one hand, resolution is limited by the plate-shaped detector and that, on the other hand, a relatively long exposure time is required because the radiation emitter and the detector need to be newly positioned between individual exposures. Therefore, an arrangement of this kind is suitable for screening tests only to a limited extent.

BRIEF SUMMARY OF THE INVENTION

The following description of the objective of the disclosure provided herein and the description of an embodiment of an X-ray machine for imaging a breast is not to be construed in any way as limiting the subject matter of the appended claims.

The objective of the disclosure provided herein is to design an X-ray machine which images a female breast in a diagnostically correct manner, and also rapidly, at favourable cost, and at the same time limits radiation exposure to the breast as much as possible. With this, a female patient is to be subjected to as little pain as possible resulting from compression of the breast etc., and instrument resources are to be used optimally.

An embodiment of an X-ray machine for imaging a breast of a female patient includes a gantry that is rotatable about an approximately horizontal rotation axis, wherein the X-ray machine is configured to set the gantry into continuous rotational motion for imaging the breast; an X-ray tube mounted on the gantry; an X-ray detector mounted on the gantry substantially opposite the X-ray tube; a locating device for locating the breast in a measurement field of the X-ray machine; and an advancing means for linear displacement of the gantry relative to the locating means and along the direction of the rotation axis of the gantry, with the linear displacement being effected in dependence upon the rotational motion.

BRIEF DESCRIPTION OF THE DRAWINGS

In the following, the invention is described by way of example without limitation of the general inventive concept, on examples of embodiments and with reference to the drawings.

Figure 1:
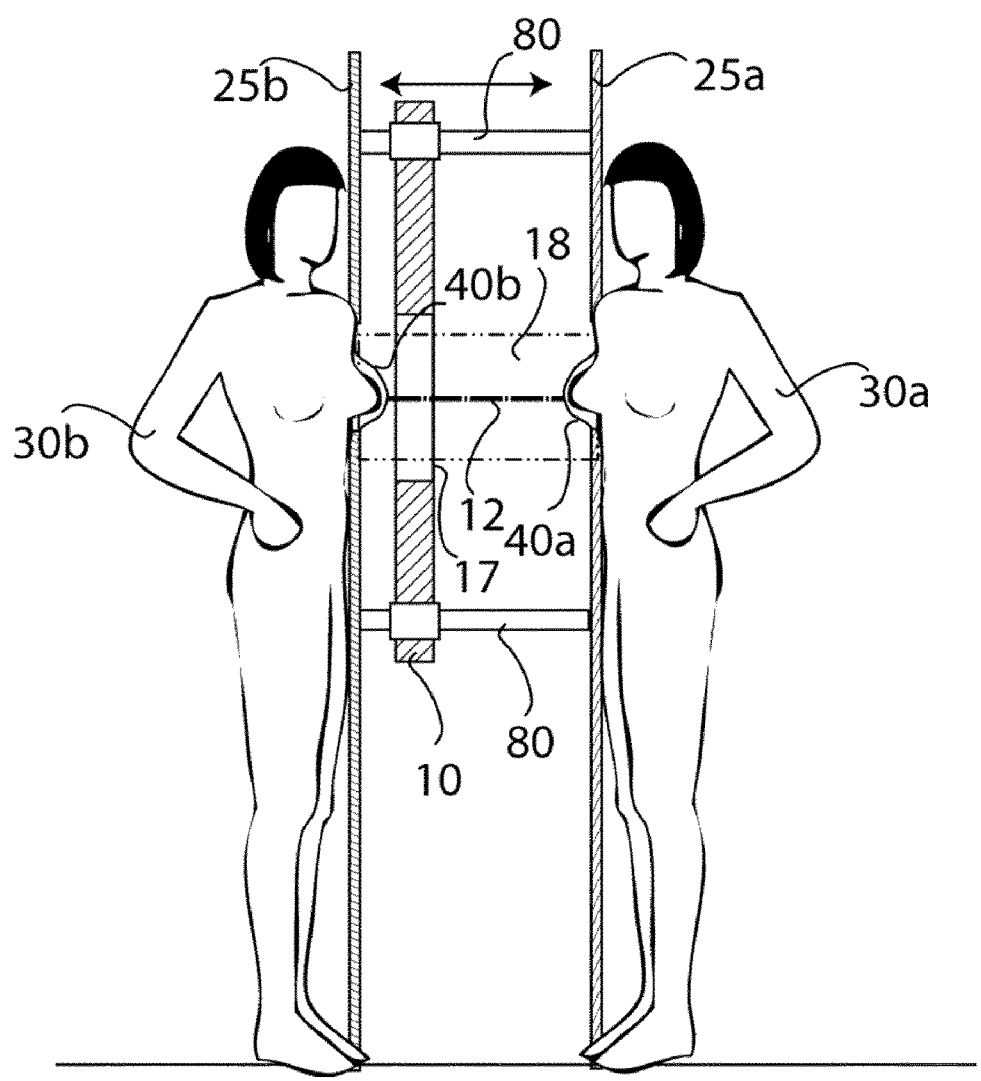
FIG. 1 shows a cross-sectional view of an example of an X-ray machine having a gantry disposed between two examination rooms.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF PREFERRED EMBODIMENTS

Figure 3:
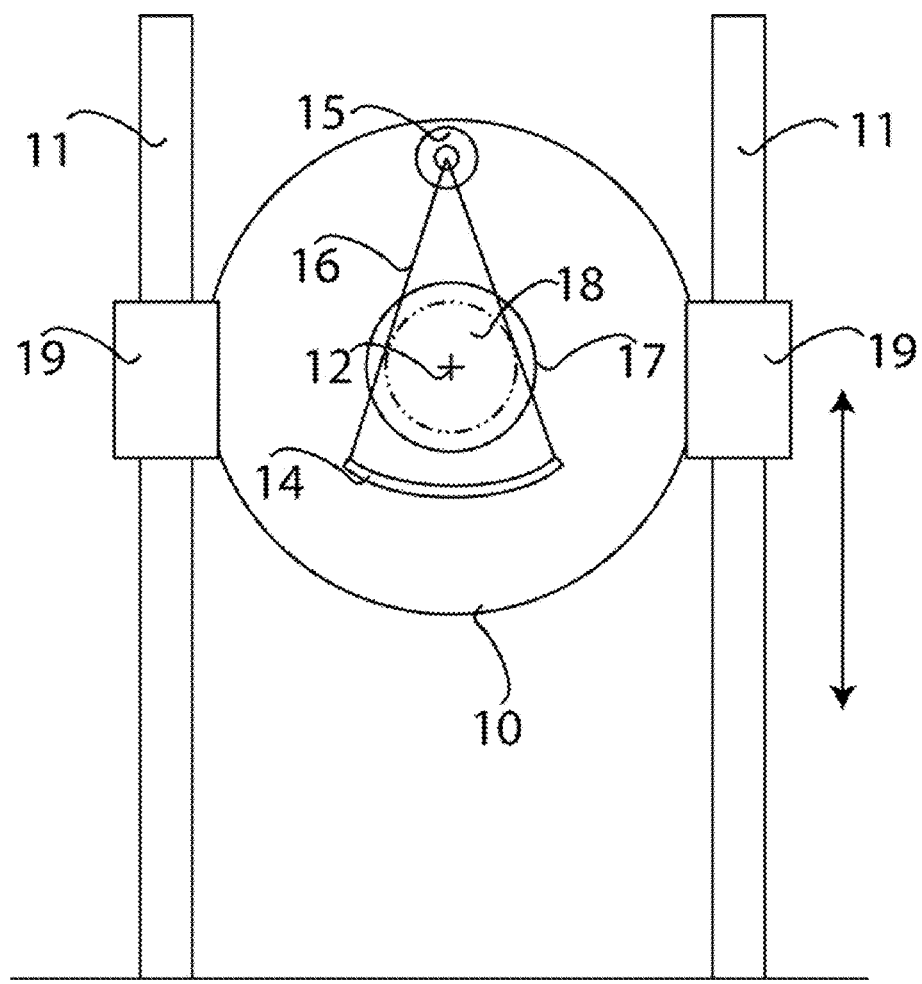
FIG. 3 shows a partial cross-sectional view of an example of an X-ray machine having a gantry of variable height.

FIG. 1 shows an example of an X-ray machine. A gantry 10 which is rotatable about a horizontal rotation axis 12 has an X-ray facility including an X-ray tube 15 and an X-ray detector 14. To simplify the drawing depicted in FIG. 1, X-ray tube 15 and X-ray detector 14 are not shown. However, the devices are shown in the partial cross-sectional view of the exemplary X-ray machine depicted in FIG. 3. It is noted that the configuration and placement of such devices described in reference to FIG. 3 are referenced for the X-ray machine depicted in FIG. 1 and are not reiterated for the sake of brevity. Referring back to FIG. 1, the gantry 10 is displaceable relative to a locating means 40a and 40b in a direction parallel to the rotation axis 12 with an advancing means 80. A displacement is effected synchronously with rotation of the gantry 10. The gantry is disposed between two examination rooms. Walls 25a and 25b facing the examination rooms are each respectively provided with a breast locating means 40a and 40b. A breast of a first patient 30a is accommodated in a locating means 40a. A breast of a second patient 30b is accommodated in a locating means 40b. It is advantageous for the walls 25a and 25b to be designed so that they screen-off radiation directed towards the patients. The first patient 30a and the second patient 30b can be examined with one machine although they are each in a separate examination room. The length of a cylindrical measurement field 18 of the X-ray machine is defined by a maximum travel of the advancing means 80, which is determined by a space between the separating walls 25a and 25b. As described in more detail below in reference to FIG. 3, the width of the cylindrical measurement field 18 may be defined relative to a dimension of the inner bore 17 of the gantry 10.

Figure 2:
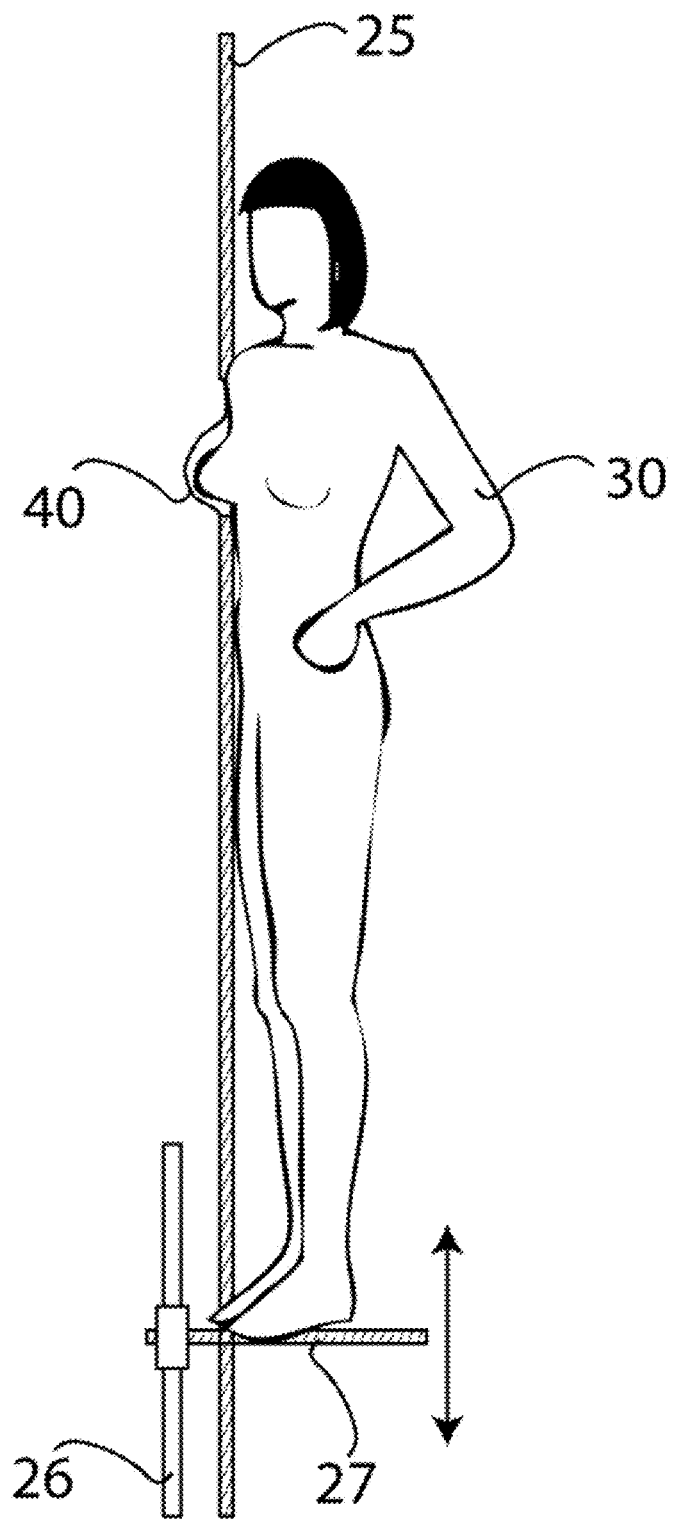
FIG. 2 shows a partial cross-sectional view of an example of an X-ray machine having a footboard of adjustable height.

FIG. 2 shows a partial cross-sectional view of an example of an X-ray machine with a footboard 27 that can be adjusted with a lift drive 26 to position a patient 30 (e.g., patient 30a or 30b of FIG. 1) in front of the wall 25 (e.g., wall 25a or 25b of FIG. 1) so that her breast can be accommodated comfortably in the breast locating means 40.

FIG. 3 shows partial cross-sectional view of an example of an X-ray machine in which the substantially disk-shaped gantry is provided with a gantry lift bearing 19. Although not shown in FIG. 3 due to the cross-sectional view chosen to show X-ray tube 15 and X-ray detector 14, it is noted that a breast locating means of the X-ray machine will further be provided with the gantry lift bearing 19. In this manner, the gantry 10 together with the breast locating means can be adjusted via a gantry lift drive 11. As noted above, the gantry itself includes the X-ray tube 15 and the X-ray detector 14. The beam path between the X-ray tube 15 and the X-ray detector 14 is illustrated by an X-ray beam 16. In this example, the X-ray beam 16 limits the diameter of a cylindrical measurement field 18 to a value that is smaller than that of the inner bore 17 of the gantry.

Figure 4:
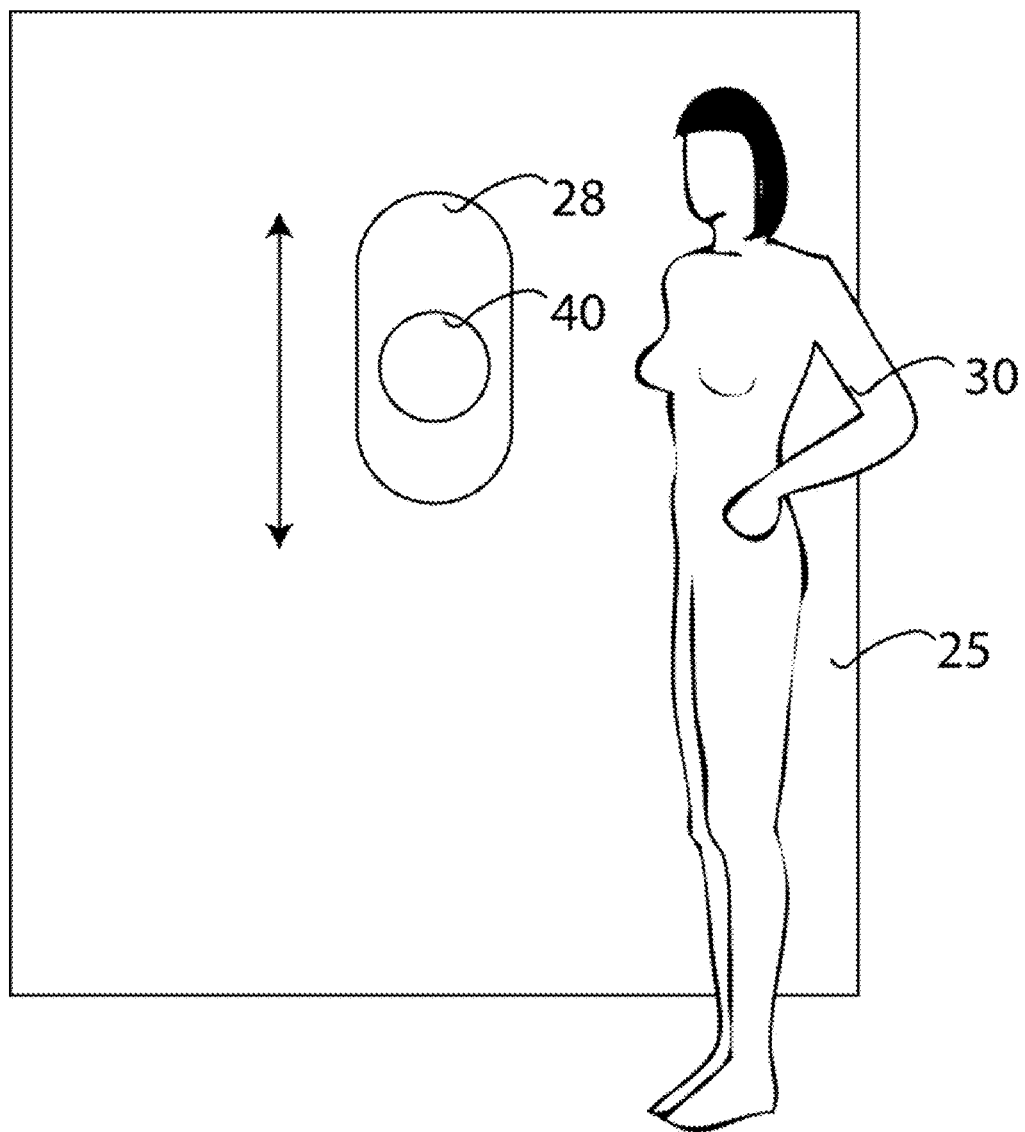
FIG. 4 shows a different cross-sectional view of the X-ray machine depicted in FIG. 3.

FIG. 4 shows the X-ray machine of FIG. 3 in a different cross-sectional view, with wall 25 having a cut out wall portion 28, so that the breast locating means 40 is accessible at any set height.

As noted above, an X-ray machine for imaging a female breast comprises a gantry 10 that is rotatable about a rotation axis 12. Mounted on this gantry is an X-ray facility with an X-ray tube 15 and also an X-ray detector 14. The X-ray tube 15 emits X-rays along a direction towards the X-ray detector 14. Locating means 40a and 40b are disposed at ends of cylindrical measurement field 18. Locating means 40a and 40b each serve to accommodate or locate a female breast. For imaging the breasts, the gantry rotates about the rotation axis. At the same time a linear displacement between the gantry 10 and the breasts held in the locating means 40a and 40b is effected by the advancing means 80. In this manner, the breasts held in the locating means 40a and 40b are disposed, at different points in time, in a beam path between the X-ray tube 15 and the X-ray detector 14. Optionally, the breasts held in the locating means 40a and 40b can be shifted relative to the gantry 10. However, it is of particular advantage for the positions of the breasts not to be changed, and for the gantry 10, therefore, to be shifted relative to the breasts held in the locating means 40a and 40b. The direction of movement is preferably parallel to the rotation axis 12 of the gantry. The movement can be effected optionally to be continuous at constant speed, or proportional to the rotation of the gantry. Alternatively, the movement also can be effected stepwise, so that, for example, a displacement amounting to a width of the detector is effected following each revolution of the gantry.

The measurement field of the X-ray machine can be defined by the inner bore 17 of the gantry and by the range in which the gantry 10 can be displaced by the advancing means 80. This measurement field is of a cylindrical shape. The range of a breast to be examined must project into the measurement field.

Owing to the design of the X-ray machines described herein, it is not necessary to use a large-area detector which can image an entire breast. Rather than this, a smaller X-ray detector 14 which has a substantially shorter width along a direction parallel to the rotation axis 12 than the length of a breast in the locating means 40a or 40b is adequate. Thus, an X-ray detector 14 having a substantially larger resolution can be used. Three-dimensional data of high diagnostic information content can be generated. A recording technique which is advantageous is the spiral CT technique. Here, the measurement field is scanned with a spiral movement, whereby complete imaging can be performed within a few seconds. With this, it is also possible to reduce substantially the time needed per person to be treated.

Locating means 40a and 40b each have at least one opening for receiving a female breast. It is advantageous to perform fastening or stabilizing of the breast with the aid of a cup or bell-shaped vessel in which a breast can be held by sub-pressure. However, other methods of fastening using rings, cords, mechanical or adhesive devices are also possible. In either case, the locating means is designed so that a principal axis of a breast, formed by a plane perpendicular to the chest wall and the nipple, extends horizontally along the rotation axis of the gantry. As discussed in reference to FIG. 1, the X-ray machines described herein may, in some embodiments, include two locating means respectively disposed relative to each side of the gantry. With this arrangement, a breast positioned in a locating means can be already imaged whilst another breast is being positioned in a second locating means. With this, an almost continuous operation of the X-ray facility on the gantry is possible. Thus, efficient screening tests can be performed. The locating means are preferably exchangeable. Thus, each locating means can be adapted to the size of a breast of a person to be examined, and/or exchanged following an examination.

In some embodiments, an X-ray machine may be disposed behind a single thin wall which adjoins an examination room. In alternative embodiments, however, one examination room can be located on each of the two sides of an X-ray machine, the one examination room being closed off from the X-ray machine by one more thin walls. In yet other embodiments, as described in reference to FIG. 1, an X-ray machine may be disposed between distinct walls which adjoin different examination rooms. In such a scenario, the gantry can now be moved with the advancing means between one part of the locating means assigned to a first examination room and a second part of the locating means assigned to a second examination room. In any of such cases, only the locating means of the X-ray machine is/are visible from the examination room/s.

The X-ray machines described herein may be fitted with a pedestal for setting-up the machine on a floor, or with a wall fastening for mounting the machine on a wall.

In addition or alternatively, the gantry 10 is of adjustable height, so that it can be adapted to various body sizes of persons to be examined. In order to make possible a simple adjustment of height, a compensation of weight by springs or counterbalancing weights may be provided. In some embodiments, an adjustment of height may be effected with a lifting device, such as with a motor and more specifically with an electric motor.

In some cases, it may be advantageous to provide a footboard 27 or step of adjustable height, on which a person to be examined can stand. The height of this footboard can be adjustable with a lifting device, such as a motor, and more specifically with an electric motor.

It is special advantage for a breast to be fastened in the locating means using sub-pressure or vacuum. An undesired compression of a breast is thereby avoided.

In some embodiments, the X-ray machine may be a spiral CT instrument. In some embodiments, the X-ray machine may be a sequential CT instrument. In such an instrument, the gantry makes circular scans and is laterally moved by the gantry lift drive after completion of a circle.

It will be appreciated to those skilled in the art having the benefit of this disclosure that this invention is believed to provide X-ray machines for imaging a breast. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

The invention claimed is:

1. An X-ray machine for imaging a breast of a female patient, comprising:
    a gantry that is rotatable about an approximately horizontal rotation axis, wherein the X-ray machine is configured to set the gantry into continuous rotational motion for imaging the breast;
    an X-ray-tube mounted on the gantry;
    an X-ray detector mounted on the gantry substantially opposite the X-ray tube;
    a locating means for locating the breast in a measurement field of the X-ray machine, wherein the locating means comprises a first locating means disposed on a first side of the gantry, and wherein the X-ray machine further comprises a second locating means disposed on a second side of the gantry opposite to the first side and the first locating means so that breasts of different patients can be inserted on each side of the gantry; and
    an advancing means for linear displacement of the gantry relative to the locating means and along a direction of the rotation axis of the gantry, with the linear displacement being effected in dependence upon the rotational motion.

2. The X-ray machine according to claim 1, further comprising a means for at least one of fastening and stabilizing a breast in the locating means using vacuum or sub-pressure.

3. The X-ray machine according to claim 1, further comprising a stand for setting-up the X-ray machine on a floor.

4. The X-ray machine according to claim 1, further comprising a wall holder for mounting the X-ray machine on a wall.

5. The X-ray machine according to claim 1, further comprising a separating wall disposed between the gantry and an area in which a patient stands to be examined, wherein the separating wall comprises a cut-out portion through which a breast can be inserted into the locating means.

6. The X-ray machine according to claim 5, wherein the locating means is incorporated in the separating wall.

7. The X-ray machine according to claim 1, wherein a height of the gantry is adjustable.

8. The X-ray machine according to claim 7, comprising a lifting device for adjustment of the height of the gantry.

9. The X-ray machine according to claim 8, wherein the lifting device comprises a motor.

10. The X-ray machine according to claim 1, further comprising a footboard of adjustable height.

11. The X-ray machine according to claim 1, wherein the X-ray machine is a spiral CT instrument.

12. The X-ray machine according to claim 1, wherein the X-ray machine is a sequential CT instrument.

13. An X-ray machine for imaging a breast of a female patient, comprising:
    a gantry that is rotatable about a substantially horizontal rotation axis;
    an X-ray tube mounted on the gantry;
    an X-ray detector mounted on the gantry opposite the X-ray tube;
    a breast receiving area disposed in a measurement field of the X-ray machine and in substantial alignment with the substantially horizontal rotation axis;
    a second breast receiving area disposed on a second side of the gantry opposite to the first side such that breasts of different patients can be inserted on each side of the gantry; and,
    wherein the X-ray machine is configured to:
        set the gantry into continuous rotational motion for imaging the breast; and
        linearly displace, in dependence upon the rotational motion, the gantry relative to the breast receiving area along a direction of the rotation axis of the gantry.

14. The X-ray machine according to claim 13, wherein the X-ray machine is disposed behind a wall of an examination room.

15. The X-ray machine according to claim 13, wherein the X-ray machine is disposed between walls of two examination rooms.

16. The X-ray machine according to claim 13, wherein the breast receiving area comprises a vessel configured to accommodate a breast.

17. The X-ray machine according to claim 13, wherein a height of the gantry is adjustable.

18. The X-ray machine according to claim 13, further comprising a footboard of adjustable height.

* * * * *

UNITED STATES PATENT AND TRADEMARK OFFICE
CERTIFICATE OF CORRECTION

| | |
|---|---|
| PATENT NO. | : 7,924,974 B2 |
| APPLICATION NO. | : 12/401735 |
| DATED | : April 12, 2011 |
| INVENTOR(S) | : Kalender et al. |

It is certified that error appears in the above-identified patent and that said Letters Patent is hereby corrected as shown below:

Claim 13 at col. 6, line 18: After "rotation axis" please add --, wherein the breast receiving area is disposed on a first side of the gantry--.

Signed and Sealed this
Twenty-fourth Day of January, 2012

David J. Kappos
*Director of the United States Patent and Trademark Office*